United States Patent
Arash (10) Patent No.: US 11,918,827 B2
(45) Date of Patent: Mar. 5, 2024

(54) ORAL HEATING APPARATUS FOR GUM DISEASE TREATMENT

(71) Applicant: Ahmad Reza Arash, Newburyport, MA (US)

(72) Inventor: Ahmad Reza Arash, Newburyport, MA (US)

(73) Assignee: GUMGENII ENTERPRISES, INC., Newburyport, MA (US)

( * ) Notice: Subject to any disclaimer, the term of this patent is extended or adjusted under 35 U.S.C. 154(b) by 0 days.

(21) Appl. No.: 16/884,915

(22) Filed: May 27, 2020

(65) Prior Publication Data
US 2021/0370092 A1     Dec. 2, 2021

(51) Int. Cl.
*A61N 5/06*     (2006.01)

(52) U.S. Cl.
CPC ......... *A61N 5/0624* (2013.01); *A61N 5/0603* (2013.01); *A61N 2005/0606* (2013.01); *A61N 2005/0632* (2013.01); *A61N 2005/0645* (2013.01)

(58) Field of Classification Search
CPC ................ A61N 5/0624; A61N 5/0603; A61N 2005/0632; A61N 2005/0606; A61N 2005/0645
See application file for complete search history.

(56) References Cited

U.S. PATENT DOCUMENTS

| | | |
|---|---|---|
| 1,539,143 A | 5/1925 | Petry |
| 3,845,558 A | 11/1974 | Kelly |
| 5,692,523 A * | 12/1997 | Croll ............. A63B 71/085 128/859 |
| 8,591,227 B2 | 11/2013 | Levine |
| 10,758,329 B1 * | 9/2020 | Wright, III ........ A61M 37/0092 |
| 2007/0259310 A1 * | 11/2007 | Goodson ............ A61N 5/0603 433/29 |
| 2008/0008978 A1 * | 1/2008 | Conrad .................. A61C 19/06 433/32 |
| 2014/0087332 A1 * | 3/2014 | Ueda ..................... B29C 43/203 264/16 |
| 2016/0001160 A1 * | 1/2016 | Engel .................. A63B 71/085 128/861 |
| 2018/0117326 A1 * | 5/2018 | Hulings ............... A61N 1/3625 |

(Continued)

FOREIGN PATENT DOCUMENTS

| | | |
|---|---|---|
| CN | 207591115 U | 7/2018 |
| DE | 20203558 U1 | 6/2004 |

(Continued)

OTHER PUBLICATIONS

Olayemi AB. Assessment and determination of human mandibular and dental arch profiles in subjects with lower third molar impaction in Port Harcourt, Nigeria. Ann Maxillofac Surg 2011;1:126-30 (Year: 2011).*

*Primary Examiner* — Rex R Holmes
*Assistant Examiner* — Shreya Anjaria
(74) *Attorney, Agent, or Firm* — Hayes Soloway PC (57) ABSTRACT

The present invention is an oral heating element designed to apply heat and increase blood circulation along the gums to prevent and treat gum disease. The oral heating apparatus is designed to fit inside the mouth for extended periods of time. The heating element has a heating filament encased in a food safe plastic sheath capable of transmitting heat evenly along the surface of the sheath facing the gums.

9 Claims, 6 Drawing Sheets

(56) References Cited

U.S. PATENT DOCUMENTS

| | | | | |
|---|---|---|---|---|
| 2018/0263746 A1* | 9/2018 | Demarest | ............. | A61N 5/0603 |
| 2020/0155276 A1* | 5/2020 | Cam | ....................... | A61F 7/007 |
| 2020/0398014 A1* | 12/2020 | Petrochenko | ......... | A61M 16/16 |
| 2021/0244965 A1* | 8/2021 | Nikinmaa | .......... | A61K 41/0057 |
| 2021/0282953 A1* | 9/2021 | Sakuma | ................... | A61F 4/00 |

FOREIGN PATENT DOCUMENTS

| | | | | |
|---|---|---|---|---|
| FR | 2641965 A1 | | 10/1997 | |
| KR | 20200136269 A | * | 12/2020 | |
| WO | WO-2020047659 A1 | * | 3/2020 | ............... A61N 1/40 |

* cited by examiner

ORAL HEATING APPARATUS FOR GUM DISEASE TREATMENT

BACKGROUND OF THE INVENTION

1. Field of the Invention

The present invention relates generally to treatments for gum disease. Particularly, the present invention relates to an oral heating element.

2. Description of the Prior Art

Gum disease is an inflammation of the gums that can progress to affect the bone that surrounds and supports teeth. It is believed to be caused by the bacteria in plaque, a sticky, colorless film that constantly forms on teeth. If not removed through daily brushing and flossing, plaque can build up and the bacteria infect not only gums and teeth, but eventually the gum tissue and bone that support the teeth. This can cause the effected teeth to become loose, fall out, or have to be removed by a dentist. There are three stages of gum disease: gingivitis, periodontitis, and advanced periodontitis.

Gingivitis is the earliest stage of gum disease, and involves an inflammation of the gums caused by plaque buildup at the gumline. If daily brushing and flossing do not remove the plaque, it produces toxins (poisons) that can irritate the gum tissue, causing gingivitis. A patient with gingivitis may notice some bleeding during brushing and flossing. At this early stage in gum disease, damage can be improved, since the bone and connective tissue that hold the teeth in place are not yet affected.

Periodontitis is the second stage. At this stage, the supporting bone and fibers that hold your teeth in place are irreversibly damaged. A patient's gums may begin to form a pocket below the gumline, which traps food and plaque. Proper dental treatment and improved home care can usually help prevent further damage.

Advanced Periodontitis is the final stage of gum disease. In this stage, the fibers and bone supporting a patient's teeth are destroyed, which can cause teeth to shift or loosen. This can affect a patient's bite and, if aggressive treatment is not possible, the teeth may need to be removed.

It is known that good oral health will help keep plaque from building up. According to the prior art, the early stages of gum disease can only be improved with proper brushing and flossing. It is also known that a professional cleaning by a dentist or hygienist is the only way to remove plaque that has built up and hardened into tartar. A dentist or hygienist may clean or "scale" your teeth to remove the tartar above and below the gumline. If a condition is more severe, a root planing procedure may be performed. Root planing helps to smooth irregularities on the roots of the teeth making it more difficult for plaque to deposit there.

While not related to methods of treating gum disease, there are technologies that exist that are similar to the present invention which will now be discussed. Chinese Patent No. 207591115, discloses a graphite alkene heating face mask providing intensifying heat evenly over the whole face. The face mask has a high conversion efficiency with transparent flexible bending mount pads.

U.S. Pat. No. 8,591,227 discloses a mouthpiece for teeth whitening which has a series of super bright light emitting diodes (LEDs) and heat generating resistors which are arrayed on an inner, lingual side of the flexible circuit board along the teeth. An inward tilt of the inner surface allows the seal bead to provides a barrier seal to both retain the whitening gel and to prevent oxygen from entering the treatment area of the tooth, separate the treatment area of the tooth from the gum above the tooth.

SUMMARY OF THE INVENTION

It is an object of the present invention to take advantage of the fact that fever is a cardinal response to infection that has been conserved in warm and cold-blooded vertebrates for over 600 million years of evolution. The fever response is known to be executed by integrated physiological and neuronal circuitry and confers a survival benefit during infection. Indeed, there is mounting evidence that the increase of 1 to 4° C. in core body temperature that occurs during fever is associated with improved survival and resolution of many infections.

Specifically, the present invention seeks to take advantage of the inflammatory cues delivered by the thermal element of fever which stimulate innate and adaptive immune responses. By providing an external thermal element which increases a localized body temperature of the infected gums, it is believed that this will also stimulate and improve the innate and adaptive immune responses of the infected gums.

It is an object of the present invention to provide a further self-treatment option for gum disease which may be used by a patient in the privacy of their own home while comfortably sleeping or engaged in other activities. It is another object of the present invention to provide a heating element capable of heating infected gums without heating the crown portion of teeth.

It is a further object of the present invention to provide an oral heating element designed to apply heat and increase blood circulation around the gums to prevent and treat gum disease. The apparatus is similar in shape to conventional mouth guards in that the mouthpiece is designed to fit comfortably inside the mouth for extended periods of time. However, the apparatus is unlike mouth guards in that the heating element is not designed to extend between the upper and lower sets of teeth. Instead, the heating element extends along the outer surface of the upper and lower sets of gums between the teeth and the lips and cheeks of a wearer. The apparatus has a heating element incased in a food safe plastic sheath with heating gel capable of transmitting heat evenly along the surface of the sheath facing the gums. An electric cord extends from the sheath to a battery pack or other electric source capable of providing electric power for at least eight hours of continual use.

The invention achieves these and other objectives by providing an oral heating element for treatment of inflammation of a patient's gums having a mouthpiece which has an upper wall, a lower wall, and two side walls. The upper wall, the lower wall, and the two side walls are integrally formed with one another. At least one window has a corresponding border which frames the window. The window is formed by the upper wall, the lower wall, and the two side walls. An energy adaptor is formed in one of the upper wall, the lower wall, and the two side walls. At least one heating filament has a leading edge connected to the energy adaptor and a trailing edge disparate from the leading edge.

The upper wall, the lower wall, and the two side walls may have an external peripheral edge, such that when a first one of the two side walls is bent backwards towards a second one of the two side walls, an angle of curvature of the mouthpiece is 180 degrees. The upper wall, the lower wall, and the two side walls may have a thickness of between 0.2 mm and 0.4 mm. The at least one heating filament may have a thickness of between 0.1 mm and 0.3 mm. The mouthpiece, extending from a first edge of the first side wall to a second edge of the second side wall opposite the first side wall, may have a length of between 12 cm and 30 cm. The oral heating element may have a detachable cord adaptor and rechargeable power source.

The mouthpiece of the oral heating element may also have interior walls which extend along an interior portion of the patient's gums as well as exterior walls which extend along an exterior portion of the patient's gums. The first side wall and the second side wall of the mouthpiece integrally connect the interior walls and the exterior walls.

The first side wall and the second side wall each further comprising: a first vertically extending portion connecting the respective exterior upper wall and the respective exterior lower wall; a second vertically extending portion connecting the respective interior upper wall and the respective interior lower wall; and a third laterally extending portion connecting the first vertically extending portion and the second extending portion; whereby the respective interior upper wall and the respective interior lower wall, the first and second side walls are integrally formed with one another.

BRIEF DESCRIPTION OF THE DRAWINGS

FIG. 12 is an upper front perspective view of the embodiment shown in FIG. 10a.

DETAILED DESCRIPTION OF THE INVENTION

Figure 1:
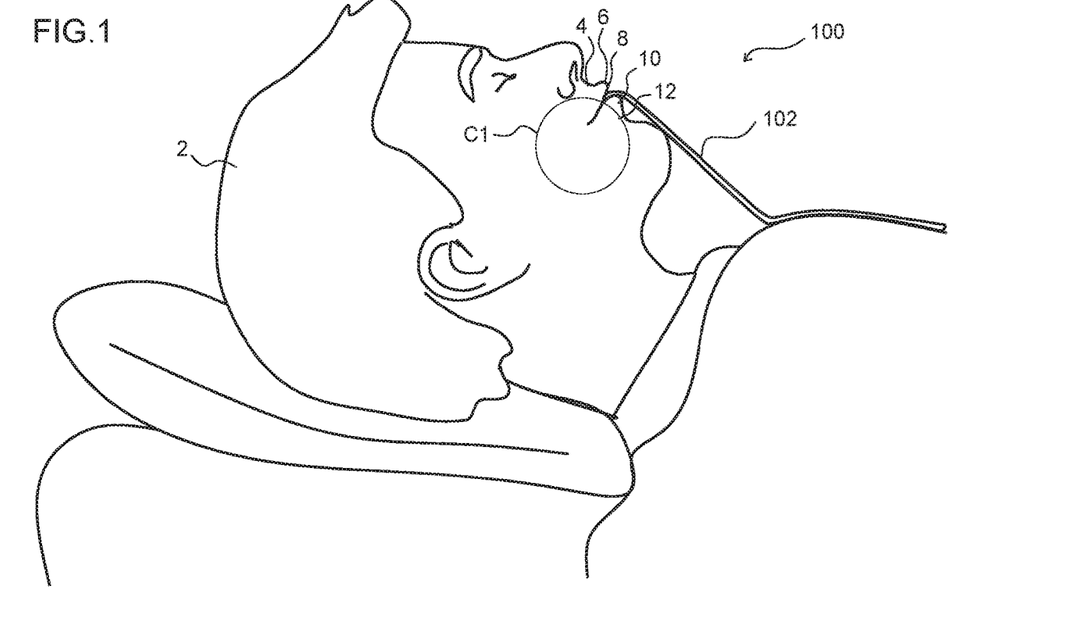
FIG. 1 is a perspective view of one embodiment of the heating element of the present invention in use by a patient.
Figure 2:
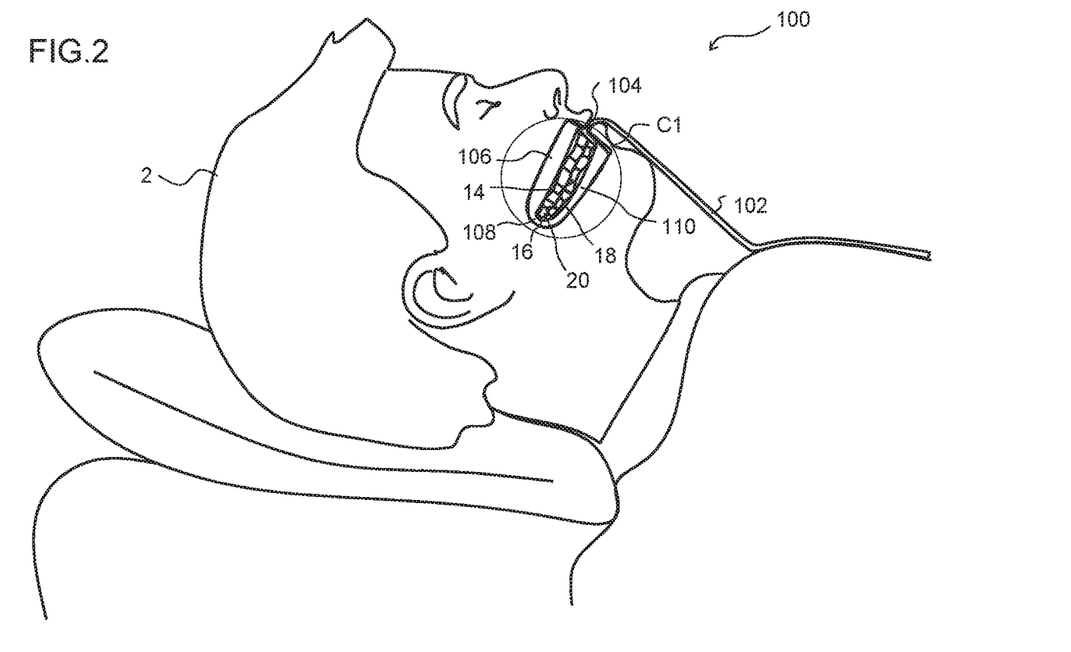
FIG. 2 is a perspective view of illustrating a partial cross-section of FIG. 1.
Figure 3:
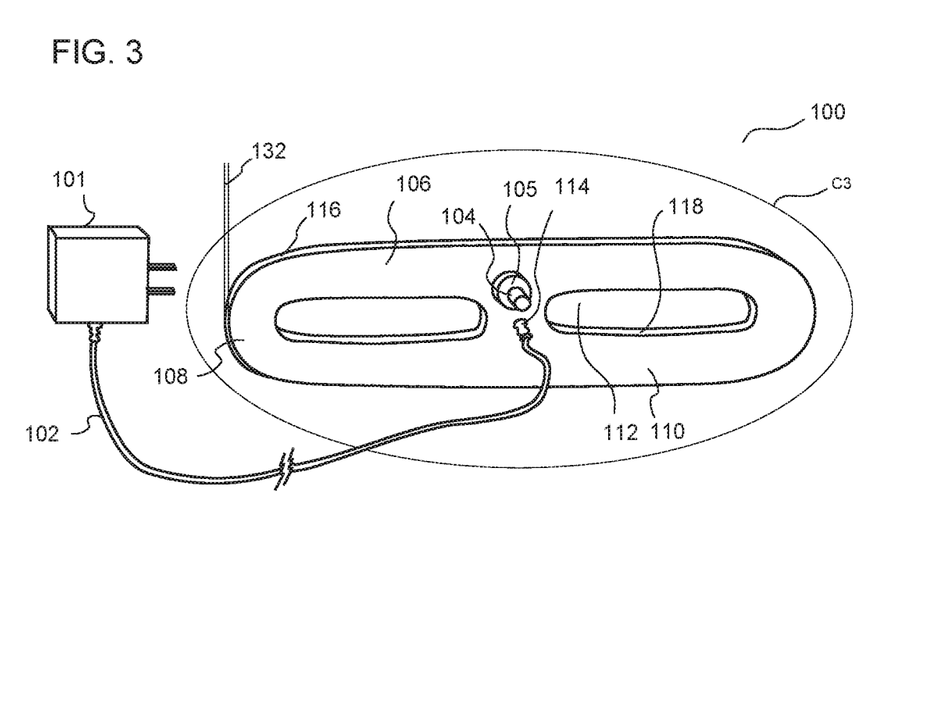
FIG. 3 is a further front perspective view of the embodiment shown in FIG. 1.
Figure 4:
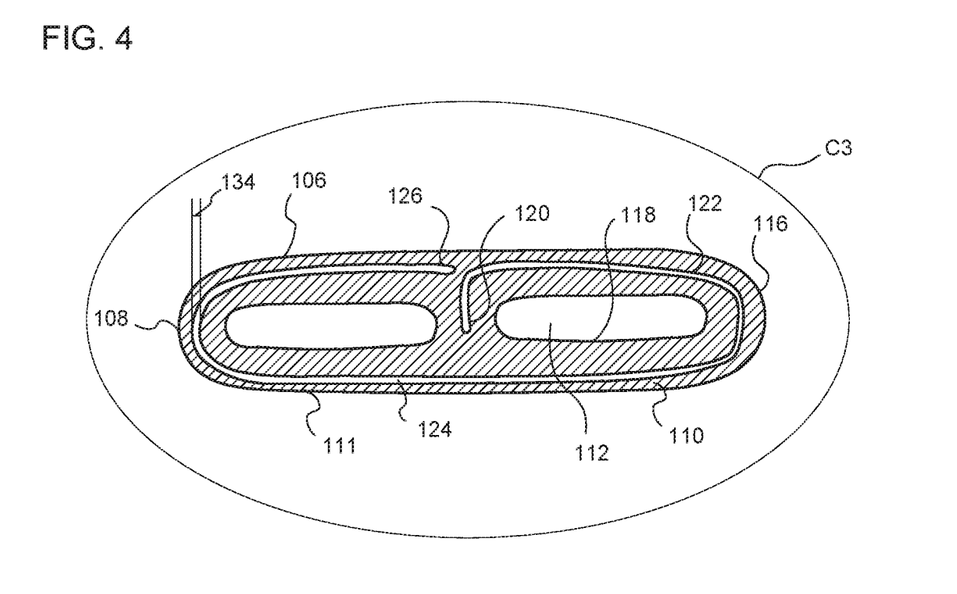
FIG. 4 is a partial frontal cross-section of the embodiment shown in FIG. 3 and FIG. 1.
Figure 5:
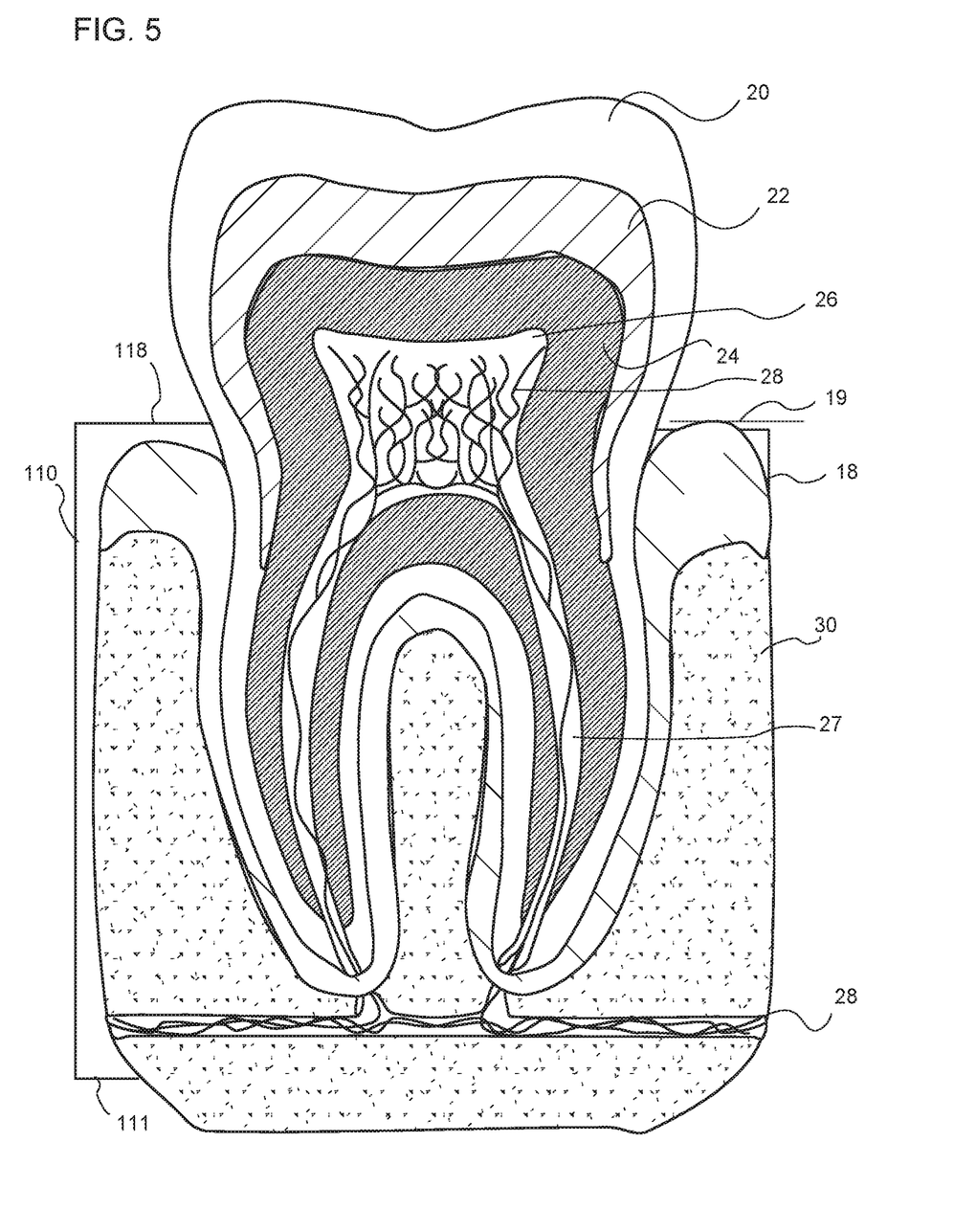
FIG. 5 is an enlarged partial frontal cross-section of the embodiment shown in FIG. 1 as in use by a patient.

A first embodiment of the present invention is illustrated in FIGS. 1-5. FIG. 1 shows a perspective view of this first embodiment of the heating element 100 of the present invention in use by a patient or other user 2. FIG. 2 is a perspective view which illustrates a partial cross-section C1 of FIG. 1, which shows how the heating element 100 fits within the oral cavity 8 of a user 2. FIGS. 3 and 4 illustrate various components of the heating element 100. FIG. 5 illustrates an enlarged partial frontal cross-section of the embodiment shown in FIG. 1 as in use by a patient.

As shown in these figures, the present invention is an oral heating element 100 has several basic components to fit the overall concept: to apply heat and increase blood circulation along the gums to prevent and treat gum disease. The oral heating apparatus 100 is designed to fit inside a user's mouth for extended periods of time. Most embodiments of the heating apparatus 100 then have a heating filament 120 encased in a food safe plastic sheath 110 capable of transmitting heat evenly along the surface of the sheath facing the gums of the patient.

When in use, an upper wall 106 of the sheath fits under the upper lip 6 and the philtrum 4, along the upper gingiva/gums 14. A lower wall 110 of the heating apparatus 100 fits under the lower lip 10 and mentolabial sulcus 12 along the lower gum 18. The walls 106, 108, 110 form a pair of windows 112 which leave the crown 20 portion of the patient's teeth exposed.

The partial cross-section illustrated in FIG. 5 shows the position of the lower wall 110 of the heating element 100 with respect to a single tooth under the lower lip 10. As shown here, the crown 20 of the tooth is exposed to the air through the window 112. Thus, the window 112 has a total height of between 15 mm and 35 mm, and more preferably, in a range of 20 to 22 mm, so that the crown 20 of both the upper and lower teeth are exposed to the air.

To facilitate this, the internal peripheral wall 118 of the window 112 extends proximate to or along the upper portion or gumline 19 of the gums 18. In this way, an upper portion of the enamel 22, reflecting the majority of the enamel 22, is above the gumline 19 (see, for example, FIG. 5). An upper portion of the dentin 24 and an upper portion of the pulp cavity 26 is also above the gumline 19.

However, the height of the lower wall 110 is such that the majority of the blood and nerve vessels 28, both extending through the root canal (lower pulp cavity 26) and the bone 30, are coplanar with the lower wall 110, and extend below the window edge 118 of the heating element 100. The height of the lower wall 110 should not extend so low into the junction between the internal cheek surface and the lower gum wall of a patient 2 causing discomfort. However, the height of the lower wall 110 should be such that, when used, the lower peripheral edge 111 of the lower wall 110 extends below the average position of the blood and nerve vessels 28 extending through the lower portion of the jawbone 30 of a user 2. This ensures the maximum amount of increased thermal activity along the blood and nerve vessels 28 thereby increasing the likelihood of stimulating and improving the innate and adaptive immune responses of the infected gums 18 of the user 2.

While shown in use while sleeping with an electrical cord 102 extending between the mouthpiece and the AC adaptor 101. A detachable cord adaptor 114 allows reversible engagement with the female cord adaptor 104 which leads to a rechargeable button battery 115. This allows a user 2 to use the mouthpiece for intermittent smaller periods of time during the day as well as when plugged in during the night for extended periods of time.

A leading edge 120 of the heating filament contacts the battery 115 and is integral with an upper portion 122 of the heating filament which extends along an upper wall 106. A vertically extending portion of the heating filament extends along a first rear wall 108 and then a horizontally extending portion 124 of the heating filament extends along a lower wall 110. A second vertically upward extending portion of the heating filament then extends along a second rear wall 108 and then a final horizontally extending upper portion 122 of the heating filament extends along the upper wall 106 until ending in the trailing portion 126 of the heating filament.

A preferred material for forming the walls 106, 108, 110 of the heating element 100 may be a plastic such as ENGAGE™ 8804 Polyolefin Elastomer produced by Dow. Inc., or another similar food-safe plastic such as those listed under FDA Drug Master File 4251. In addition to being safe for placing in the oral cavity of a user, the material must also be capable of significant flexibility. At the very least, the walls need to be capable of reaching an angle of curvature (reference number 130) of 180 degrees from a first rear wall 108 to a second rear wall 108. A thickness 132 of the walls 106, 108, 110 is between 10 mm and 2 mm, and more preferably, around 5 mm.

A preferred material for forming the heating filament may be a 28 AWG copper wire or other similar filament capable of providing heating sufficient to provide increased thermal activity in a range of between 97.9° F. (36.6° C.) to 180° F. (82° C.). More particularly in a range of between 100.4° F. (38° C.) to 135° F. (57.2° C.). A minimum temperature then being around body temperature 97.9° F. (36.6° C.)-100.4° F. (38° C.), and a maximum temperature output being of about 135° F.-180° F. (57.2° C.-82° C.). A thickness 134 of the heating filament is preferably between 2 and 0.01 mm, and more preferably, around 0.5+/−0.2 mm.

Further Embodiment—Single Window

Figure 6:
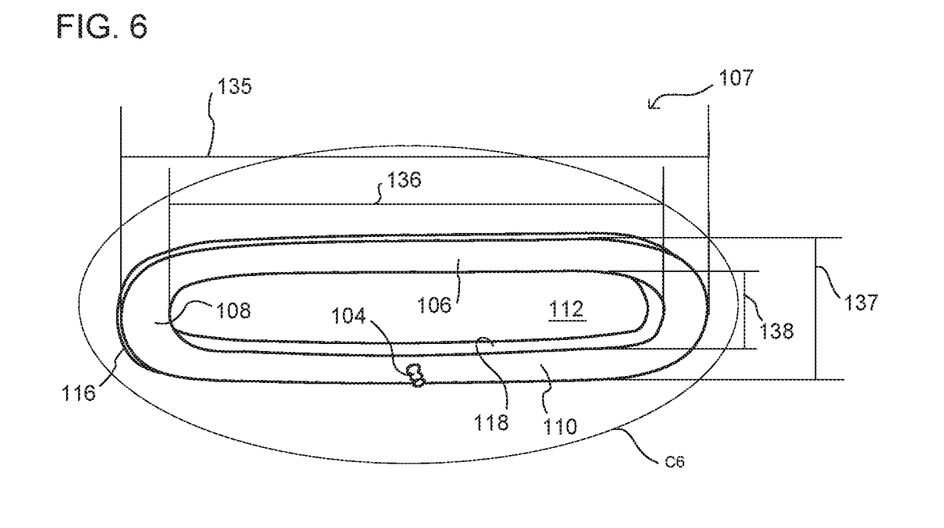
FIG. 6 is a front perspective view of a further embodiment of the heating element of the present invention.
Figure 7:
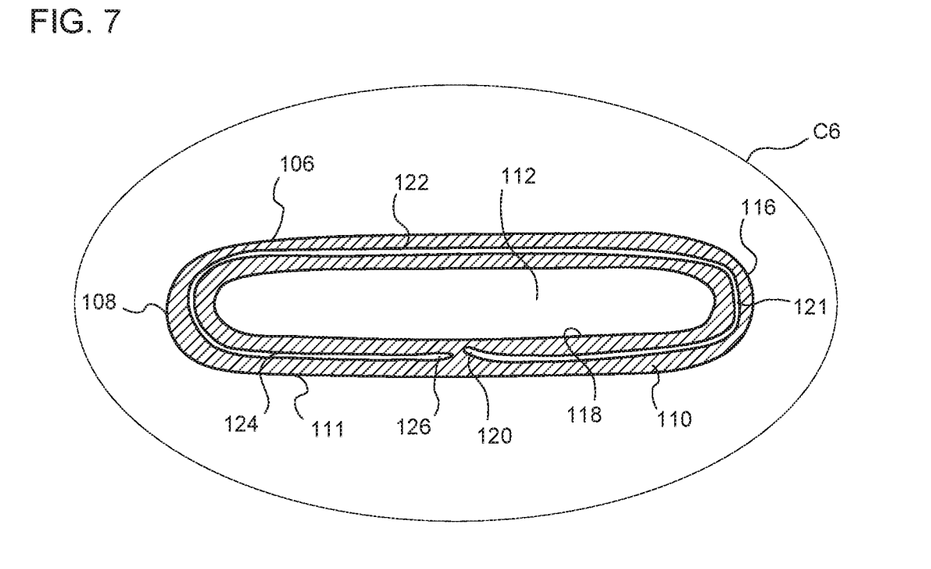
FIG. 7 is a partial frontal cross-section of the further embodiment shown in FIG. 6.

Further embodiments of the present invention are similar in most basic principles as those discussed above. A few differences in one further embodiment of the present invention will now be discussed. In this embodiment, the window 112 may extend fully from the first side wall 108 to the second side wall 108. In this embodiment, a leading edge 120 of the heating filament contacts the cord adaptor 104 directly. The leading edge 120 extends into a first lower horizontal portion 124. A vertical extending portion 125 then extends upwards into a first upper portion 122 of the heating filament which extends along the upper wall 106. A second vertically extending portion of the heating filament then extends downwards along a second rear wall 108. A second horizontally extending portion 124 of the heating filament then extends along the lower wall 110 until ending in the trailing portion 126 of the heating filament.

Further Embodiment—Multiple Windows

Figure 8:
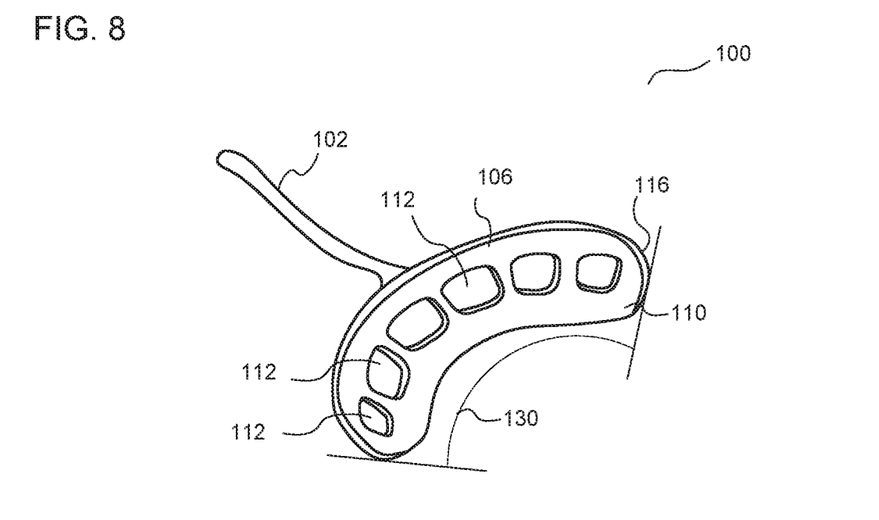
FIG. 8 is a front perspective view of a further embodiment of the heating element of the present invention.
Figure 9:
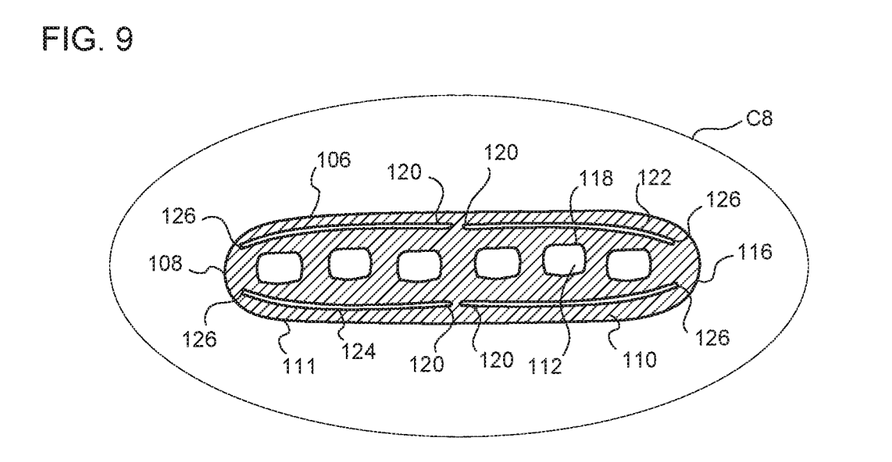
FIG. 9 is a partial frontal cross-section of the further embodiment shown in FIG. 8.

In yet another embodiment of the present invention, multiple windows 112 may extend partially between the first side wall 108 and the second side wall 108. In this embodiment, a first leading edge 120 of the heating filament contacts a first portion of the cord adaptor 104 directly. The first leading edge 120 extends into a first lower horizontal portion 124 along the lower wall 110 until ending in a first trailing portion 126 of the heating filament. A second leading edge 120 of the heating filament contacts a second portion of the cord adaptor 104 directly. The second leading edge 120 extends into a second lower horizontal portion 124 along the lower wall 110 until ending in a second trailing portion 126 of the heating filament.

A third leading edge 120 of the heating filament contacts a third portion of the cord adaptor 104 directly. The third leading edge 120 extends into a third lower horizontal portion 124 along the upper wall 106 until ending in a third trailing portion 126 of the heating filament. A fourth leading edge 120 of the heating filament contacts a fourth portion of the cord adaptor 104 directly. The fourth leading edge 120 extends into a fourth lower horizontal portion 124 along the upper wall 106 until ending in a fourth trailing portion 126 of the heating filament.

Further Embodiment—Interior and Exterior Walls

Figure 10:
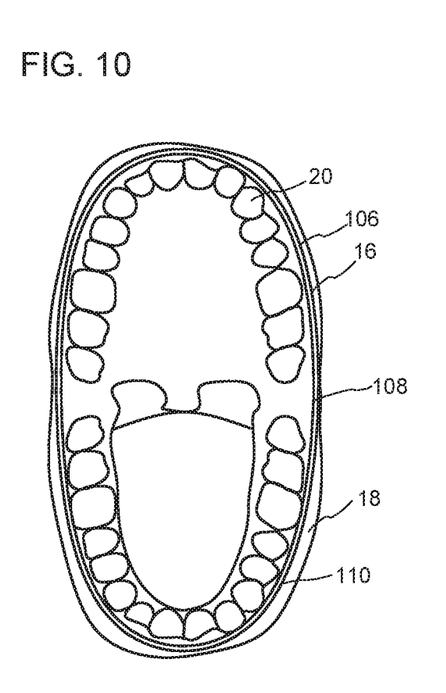
FIG. 10 is an upper perspective view of an embodiment similar to those shown in FIGS. 1-9, shown in an open mouth as worn by a user.
Figure 10A:
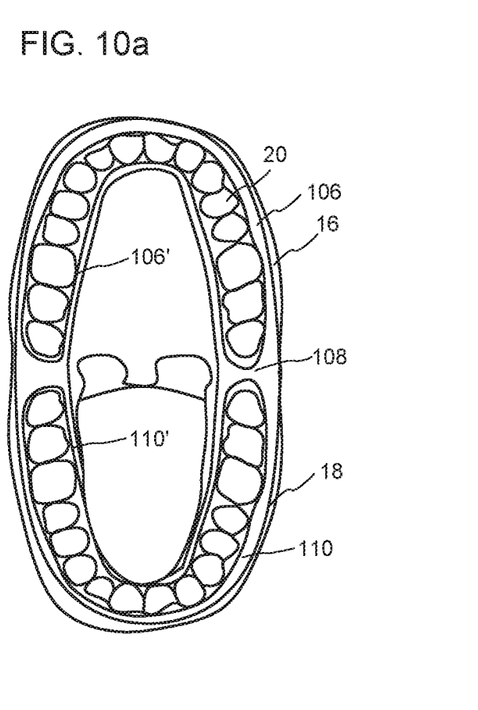
FIG. 10a is an upper perspective view of a further embodiment shown in an open mouth as worn by a user.
Figure 11:
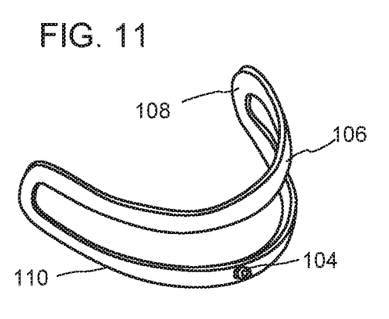
FIG. 11 is an upper front perspective view of the embodiment shown in FIG. 10.
Figure 12:
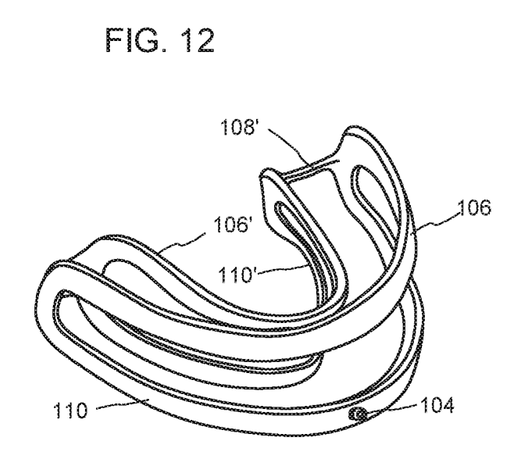

FIGS. 10-12 illustrate the differences and similarities between and among additional embodiments. For example, in previous embodiments the mouthpiece 107 has an upper wall 106 and lower wall 110 along exterior portions of the upper and lower gum 14, 18. Further embodiments additionally have an upper wall 106' and lower wall 110' along interior portions of the upper and lower gum 14', 18', which still leaves the uppermost portion of the crown 20 fully exposed as shown clearly in FIG. 10*a*.

The rear wall 108' in this embodiment has three segments. A first vertical segment extends as before between the horizontally extending upper wall 106 and lower wall 110. A second vertical segment similarly extends between the horizontally extending upper wall 106' and lower wall 110'. A third bridge segment extends laterally between the first and the second vertical segments, connecting the outer walls 106, 110 and the inner walls 106', 110'.

LIST OF REFERENCED ELEMENTS

The following reference numbers are adhered to within the specification to refer to those referenced elements within the drawings of the present application.

| | |
|---|---|
| C1 | cross-section of FIG. 1 |
| C3 | cross-section of FIG. 3 |
| C6 | cross-section of FIG. 6 |
| C8 | cross-section of FIG. 8 |
| 2 | patient/user |
| 4 | upper space above the lip |
| 6 | upper lip |
| 8 | oral cavity |
| 10 | lower lip |
| 12 | lower space above lower lip |
| 14 | upper gingiva |
| 16 | rear gingiva |
| 18 | lower gingiva |
| 20 | crown |
| 22 | enamel |
| 24 | dentin |
| 26 | pulp cavity |
| 27 | root canal |
| 28 | blood and nerve vessels |
| 30 | bone |
| 100 | Heating Element |
| 101 | AC Adaptor |
| 102 | Cord |
| 104 | Cord adaptor |
| 105 | Battery pack |
| 106 | Upper wall |
| 106' | Upper wall |
| 107 | Mouthpiece |
| 108 | Rear wall |
| 110' | Lower interior wall |
| 110 | Lower wall |
| 111 | Lowest peripheral edge |
| 112 | Window |
| 114 | Detachable cord adaptor |
| 116 | External edge of side wall |
| 118 | Peripheral window wall |
| 120 | Leading edge of heating filament |
| 121 | Vertically extending portion of heating filament |
| 122 | Upper portion of heating filament |
| 124 | Lower portion of heating filament |
| 126 | Trailing portion of heating filament |
| 130 | Angle of curvature |

| | |
|---|---|
| 132 | Width of element walls/windows |
| 134 | Width of heating filament |
| 135 | Length of heating element |
| 136 | Length of window |
| 137 | Height of Element |
| 138 | Height of window |

CONCLUSION

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. An oral heating element adapted for self-treatment of inflammation of gums of a patient, the patient having a gumline at a junction between the gums and teeth, the gums having an interior portion facing inwards and an exterior portion facing outwards, the teeth having uppermost crown portions, the oral heating element comprising:
a mouthpiece having an upper wall, a lower wall, a first side wall, and a second side wall, wherein the upper wall, the lower wall, and the first and second side walls are integrally formed with one another, wherein the upper wall, the lower wall, the first side wall, and the second side wall are exterior walls, and wherein the upper wall, the lower wall, the first side wall, and the second side wall are adapted to be positioned so as to cover the exterior portion of the gums and to expose the uppermost crown portions of the teeth; at least one border frames at least one window opening, the at least one border formed by the upper wall, the lower wall, and the first and second side walls, the at least one window extends horizontally across the teeth, and extends parallel to the gumline, and wherein the at least one border is adapted to be positioned adjacent to the gumline such that the at least one window opening extending horizontally through the mouthpiece thereby exposes the teeth;
interior walls having an interior upper wall and an interior lower wall, the interior walls adapted so as to extend along the interior portion of the patient's gums; wherein the upper wall, the lower wall, the first side wall, and the second side wall which are exterior walls adapted so as to extend along the exterior portion of the patient's gums are integrally connected to the interior walls; and wherein the first side wall and the second side wall integrally connect the interior walls and the exterior walls by rear walls disposed adjacent to the first side wall and second side wall respectively;
an energy adaptor formed in one of the upper wall, the lower wall, and the first and second side walls; and
at least one heating filament extending within at least one of the upper wall, the lower wall, and the first and second side walls, the at least one heating element comprising 28 AWG copper wire, wherein the at least one heating filament has a leading edge connected to the energy adaptor and a trailing edge disparate from the leading edge.

2. The oral heating element of claim 1 wherein the first side wall and the second side wall each further comprise: a first vertically extending portion connecting the respective exterior upper wall and the respective exterior lower wall; a second vertically extending portion connecting the respective interior upper wall and the respective interior lower wall; and a third laterally extending portion connecting the first vertically extending portion and the second extending portion; whereby the respective interior upper wall and the respective interior lower wall, the first and second side walls are integrally formed with one another.

3. An oral heating element adapted for self-treatment of inflammation of gums of a patient, the patient having a gumline at a junction between the gums and teeth, the gums having an interior portion facing inwards and an exterior portion facing outwards, the teeth having uppermost crown portions, the oral heating element comprising:
a mouthpiece having an upper wall, a lower wall, a first side wall, and a second side wall, wherein the upper wall, the lower wall, the first side wall, and the second side wall are exterior walls, and wherein the upper wall, the lower wall, the first side wall, and the second side wall are adapted to be positioned so as to cover the exterior portion of the gums and expose the uppermost crown portions of the teeth;
a plurality of borders frame a plurality of window openings, wherein the plurality of borders are formed by the upper wall, the lower wall, and the first and second side walls, wherein the plurality of window openings extend horizontally so as to be parallel to the gumline, and wherein the plurality of borders are adapted to be positioned adjacent to the gumline such that the plurality of window openings extend horizontally through the mouthpiece and thereby expose the teeth while the gums are covered;
interior walls having an interior upper wall and an interior lower wall, the interior walls adapted so as to extend along the interior portion of the patient's gums; wherein the upper wall, the lower wall, the first side wall, and the second side wall which are exterior walls adapted so as to extend along the exterior portion of the patient's gums are integrally connected to the interior walls; and wherein the first side wall and the second side wall integrally connect the interior walls and the exterior walls by rear walls disposed adjacent to the first side wall and second side wall respectively;
an energy adaptor formed in the upper wall;
at least one heating filament extending within at least one of the upper wall, the lower wall, and the first and second side walls, the at least one heating element comprising 28 AWG copper wire, wherein the at least one heating filament has a leading edge connected to the energy adaptor and a trailing edge disparate from the leading edge;
a detachable adaptor capable of reversible engagement with the energy adaptor formed within the upper wall; and
an energy source connected to the detachable adaptor.

4. The oral heating element of claim 3 wherein the upper wall, the lower wall, and the first and second side walls further comprise an external peripheral edge, and when the first side wall is bent backwards towards the second side wall, an angle of curvature of the mouthpiece is 180 degrees.

5. The oral heating element of claim 3 wherein the energy source connected to the detachable adaptor further comprises a rechargeable power source.

6. The oral heating element of claim 5 wherein the rechargeable power source is a rechargeable button battery.

7. The oral heating element of claim 6, wherein the first side wall and the second side wall each further comprise: a first vertically extending portion connecting the respective exterior upper wall and the respective exterior lower wall; a second vertically extending portion connecting the respective interior upper wall and the respective interior lower wall; and a third laterally extending portion connecting the first vertically extending portion and the second extending portion; whereby the respective interior upper wall and the respective interior lower wall, the first and second side walls are integrally formed with one another.

8. The oral heating element of claim 3 wherein the heating filament is capable of providing heating sufficient to provide increased thermal activity in a range of between 97.9° F. to 180° F.

9. The oral heating element of claim 3 wherein the heating filament is capable of providing a maximum temperature output of between 135° F.-180° F.

* * * * *